United States Patent [19]

Miller et al.

[11] Patent Number: 5,165,093
[45] Date of Patent: Nov. 17, 1992

[54] INTERSTITIAL X-RAY NEEDLE

[75] Inventors: Robert B. Miller; John R. Smith, both of Albuquerque; Carl A. Muehlenweg, Moriarty, all of N. Mex.

[73] Assignee: The Titan Corporation, San Diego, Calif.

[21] Appl. No.: 855,664

[22] Filed: Mar. 23, 1992

[51] Int. Cl.$^5$ .............................................. H01J 35/14
[52] U.S. Cl. .................................. 378/138; 378/130; 378/199; 378/202
[58] Field of Search ............... 378/119, 121, 127, 130, 378/137, 141, 143, 138, 199-202

[56]           References Cited
        U.S. PATENT DOCUMENTS

| 2,651,727 | 9/1953  | Ehrenberg et al. | 250/93  |
|-----------|---------|------------------|---------|
| 2,748,293 | 5/1956  | Reiniger         | 250/105 |
| 3,609,432 | 9/1971  | Shimula          | 378/141 |
| 3,668,454 | 6/1972  | Shimura          | 313/57  |
| 3,783,251 | 1/1974  | Pavkovich        | 235/151 |
| 3,969,629 | 7/1976  | McIntyre         | 250/503 |
| 4,157,475 | 6/1979  | Stock et al.     | 250/503 |
| 4,409,993 | 10/1983 | Furihata         | 128/784 |
| 4,763,671 | 8/1988  | Goffinet         | 128/786 |
| 4,825,880 | 5/1989  | Stauffer et al.  | 128/804 |
| 4,969,863 | 11/1990 | van't Hooft et al. | 600/3 |
| 4,993,430 | 2/1991  | Shimoyama et al. | 128/784 |
| 5,026,959 | 6/1991  | Ito et al.       | 219/10.55 A |

Primary Examiner—Janice A. Howell
Assistant Examiner—Don Wong
Attorney, Agent, or Firm—Edward W. Callan

[57]              ABSTRACT

An interstitial X-ray needle includes an elongated X-ray tube coupled to an electron emitter at one end of the tube, with a converter element being disposed at a tip of the other end of the tube for converting emitted electrons into X-ray; a solenoid coil wound around the tube for providing a magnetic field that confines the emitted electrons within a narrow beam; an elongated outer casing enclosing the tube and coil; and a pipe coaxially disposed between the casing and the tube for defining an inner annular flow chamber between the tip of the tube and a coolant inlet in the casing and an outer annular flow chamber between the tip of the tube and a coolant outlet in the casing.

6 Claims, 1 Drawing Sheet

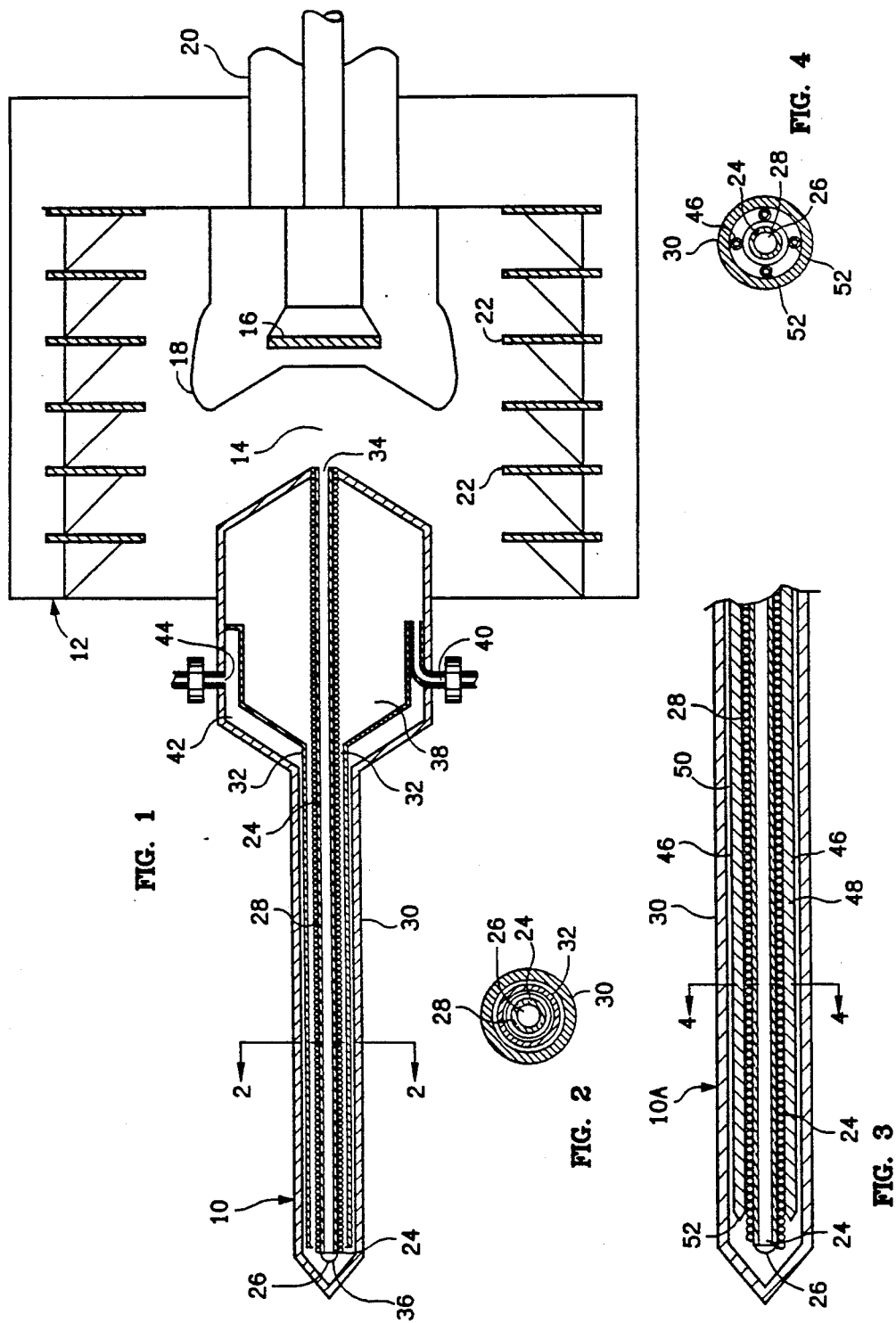

INTERSTITIAL X-RAY NEEDLE

BACKGROUND OF THE INVENTION

The present invention generally pertains to X-ray apparatus and is particularly directed to an interstitial X-ray needle.

An X-ray apparatus is used for radiation therapy of cancer patients. One such apparatus, as described in U.S. Pat. No. 2,748,293 to Reiniger, includes an elongated X-ray tube with a converter element being disposed at a tip of the tube for converting emitted electrons into X-rays; and an elongated outer casing enclosing the tube and defining a coolant flow chamber through which coolant may flow to transfer heat from the tip of the tube. The tube is inserted into a cancer patient's body through a body cavity to position the converter element so that the X-rays can be concentrated at the tumor and thereby minimize radiation damage to adjacent undiseased tissue. However, the size of such an X-ray apparatus is too large for insertion of the tube through the skin, whereby the applicability of X-ray therapy for treatment of cancerous internal body parts has been limited to only those body parts that can be accessed through body cavities.

SUMMARY OF THE INVENTION

The present invention provides an interstitial X-ray needle, comprising an elongated X-ray tube coupled to an electron emitter at one end of the tube, with a converter element being disposed at a tip of the other end of the tube for converting emitted electrons into X-rays; a solenoid coil wound the tube for providing a magnetic field that confines the emitted electrons within a narrow beam; an elongated outer casing enclosing the tube and coil; and means within the casing defining coolant flow chambers for directing coolant to and from the tip of the tube.

The interstitial X-ray needle of the present invention may be of such small diameter that a portion of the casing extending at least approximately five centimeters from the tip of the tube has a maximum outside diameter of approximately two millimeters. An X-ray needle of such diameter may be inserted in a patient's body without significant damage to tissue between the skin and the tumor site, thereby significantly increasing the applicability of X-ray therapy for treatment of cancerous internal body parts.

To prevent electron loss and stray X-radiation, the solenoid coil is wound around the beam-transport tube in order to provide a magnetic field that tightly confines the emitted electrons.

In one aspect of the present invention, the coolant-flow-chamber-defining means comprises a pipe coaxially disposed between the casing and the tube for defining an inner annular flow chamber between the tip of the tube and a first opening in the casing and an outer annular flow chamber between the tip of the tube and a second opening in the casing.

In another aspect of the present invention, the coolant-flow-chamber-defining means comprises a plurality of pipes disposed between the casing and the tube wherein each pipe defines an input flow chamber between the tip of the tube and at least one inlet opening in the casing and wherein the space between the tube and the casing not occupied by the pipes defines an output flow chamber between the tip of the tube and an outlet opening in the casing.

Additional features of the present invention are described in relation to the description of the preferred embodiment.

BRIEF DESCRIPTION OF THE DRAWING

FIG. 1 is a diagram of an X-ray apparatus including a preferred embodiment of the interstitial X-ray needle of the present invention.

FIG. 2 is a sectional view of the needle of FIG. 1 taken along lines 2—2.

FIG. 3 is a diagram of a portion of the needle illustrating an alternative preferred embodiment of the flow-chamber defining means.

FIG. 4 is a sectional view of the needle of FIG. 3 taken along lines 4—4.

DESCRIPTION OF THE PREFERRED EMBODIMENTS

Referring to FIGS. 1 and 2, an X-ray apparatus containing a preferred embodiment of the interstitial X-ray needle of the present invention includes the needle 10 and a diode housing 12 for receiving the needle. The diode housing 12 includes a vacuum chamber 14 containing an electron emitter 16 and a control grid 18. The electron emitter 16 is connected to a high voltage cable 20, which is connected to a high voltage source (not shown). Insulators 22 are stacked between the electron emitter 16 and the diode housing 12.

The needle 10 includes an elongated X-ray tube 24, a converter element 26, a solenoid coil 28, and elongated outer casing 30 and a pipe 32.

The X-ray tube 24 has an open end 34 which opens into the vacuum chamber 14 to couple the X-ray tube 24 to the electron emitter 16.

The converter element 26 is disposed at a tip 36 of the other end of the tube 24 for converting electrons emitted from the electron emitter 16 into X-rays.

The solenoid coil 28 is wound around the tube 24 for providing a magnetic field that confines the emitted electrons within a narrow beam. The electron beam can be confined to a diameter of approximately 0.4 millimeter when the solenoid coil 28 provides a magnetic field of approximately 20 gauss. For a coil 28 having 13 ohms resistance and wound at 20 turns-per-centimeter, the required current in the winding is only 0.8 amperes and the required voltage across the coil is only 0.1 volts, whereby the power expended in the winding is only 0.08 watts.

The outer casing 30 encloses the tube 24 and coil 28.

The pipe 32 is coaxially disposed between the outer casing 30 and the tube 24 for defining an inner annular flow channel 38 between the tip 36 of the tube 24 and a coolant inlet 40 in the casing 30, and an outer annular flow chamber 42 between the tip 36 of the tube 24 and a coolant outlet 44 in the casing 30.

For a needle 10 of the embodiment of FIGS. 1 and 2, including a ten-centimeter long tube 24 having an inside diameter of 0.64 millimeter and an outside diameter of 0.81 millimeter wound with a single layer of #33 magnetic wire of 0.22 millimeter diameter at approximately 40 turns-per-centimeter, an outer casing 30 having an outside diameter of 2.8 millimeters and an inside diameter of 2.16 millimeters, and a pipe of 1.52 millimeters inside diameter and 1.83 millimeters outside diameter, a water flow rate of 87 milliliters-per-minute is obtained at an inlet pressure of 20 pounds-per-square-inch, whereby for a 20 watt heat rate at the tip 36 of the needle 10, the water temperature rise over ten minutes is less than 5 degrees Celsius.

Referring to FIGS. 3 and 4, in an alternative preferred embodiment, the needle 10A includes an elongated X-ray tube 24, a converter element 26, a solenoid coil 28, an elongated outer casing 30 and a plurality of pipes 46. The pipes 46 are disposed between the casing 30 and the tube 24. Each pipe defines an input flow chamber 48 between the tip 36 of the tube 24 and at least one inlet opening (not shown) in the casing 30; and the space 50 between the tube 24 and the casing 30 not occupied by the pipes 46 defines an output flow chamber between the tip 36 of the tube 24 and an outlet opening (not shown) in the casing 30.

For a needle 10A of the embodiment of FIGS. 3 and 4, including a ten-centimeter long tube 24 having an inside diameter of 0.64 millimeter and an outside diameter of 0.81 millimeter wound with a single layer of #33 magnetic wire of 0.22 millimeter diameter at approximately 40 turns-per-centimeter, an outer casing 30 having an outside diameter of 2.8 millimeters and an inside diameter of 2.16 millimeters, and four pipes each having outlet orifice jets 52 of 0.15 millimeter directed at the tip 36 of the needle 10A, a water flow rate of 10 milliliters-per-minute is obtained at an inlet pressure of 50 pounds-per-square-inch, whereby for a 20 watt heat rate at the tip 36 of the needle 10A, the water temperature rise over ten minutes is approximately 28 degrees Celsius.

The tube 24, casing 30 and pipe 32 or pipes 46 typically are rigid and straight, but also may be made of flexibe materials or may be curved rather than straight so as to enable insertion of the tip of the needle to portions of the body that are not directly accessible through soft tissue.

The X-ray apparatus described herein may be operated at a relatively low power level of 14 watts when delivering a radiation dose of approximately 100 Gray over ten minutes duration to tissue located one centimeter from the converter element 26 by operating with an electron emitter voltage of 200 kilovolts and a beam current of 0.07 milliamperes.

In addition to providing benefits incident to its size, the miniature interstitial X-ray needle of the present invention also may generate controlled hyperthermic temperatures for application to the treated tumor, which combined with the radiation treatment may provide a synergistic healing effect.

What is claimed is:

1. An interstitial X-ray needle, comprising
   an elongated X-ray tube coupled to an electron emitter at one end of the tube, with a converter element being disposed at a tip of the other end of the tube for converting emitted electrons into X-rays;
   a solenoid coil wound around the tube for providing a magnetic field that confines the emitted electrons within a narrow beam;
   an elongated outer casing enclosing the tube and coil; and
   means within the casing defining coolant flow chambers for directing coolant to and from the tip of the tube.

2. A needle according to claim 1, wherein the flow-chamber-defining means comprises a pipe coaxially disposed between the casing and the tube for defining an inner annular flow chamber between the tip of the tube and a first opening in the casing and an outer annular flow chamber between the tip of the tube and a second opening in the casing.

3. A needle according to claim 1, wherein the flow-chamber-defining means comprises a plurality of pipes disposed between the casing and the tube wherein each pipe defines an input flow chamber between the tip of the tube and at least one inlet opening in the casing and wherein the space between the tube and the casing not occupied by the pipes defines an output flow chamber between the tip of the tube and an outlet opening in the casing.

4. An interstitial X-ray needle, comprising
   an elongated X-ray tube coupled to an electron emitter at one end of the tube, with a converter element being disposed at a tip of the other end of the tube for converting emitted electrons into X-rays;
   a solenoid coil wound around the tube for providing a magnetic field that confines the emitted electronss within a narrow beam;
   an elongated outer casing enclosing the tube and coil, wherein a portion of the casing extending at least approximately five centimeters from the tip of the tube has a maximum outside diameter of approximately two millimeters; and
   means within the casing defining coolant flow chambers for directing coolant to an from the tip of the tube.

5. A needle according to claim 4, wherein the flow-chamber-defining means comprises a pipe coaxially disposed between the casing and the tube for defining an inner flow chamber between the tip of the tube and a first opening in the casing and an outer annular flow chamber between the tip of the tube and a second opening in the casing.

6. A needle according to claim 4, wherein the flow-chamber-defining means comprises a plurality of pipes disposed between the casing and the tube wherein each pipe defines an input flow chamber between the tip of the tube and at least one inlet opening in the casing and wherein the space between the tube and the casing not occupied by the pipes defines an output flow chamber between the tip of the tube and an outlet opening in the casing.

* * * * *